United States Patent
Rubin et al.

(12) 
(10) Patent No.: US 6,172,055 B1
(45) Date of Patent: *Jan. 9, 2001

(54) APOPTOSIS INHIBITORS FOR TREATING NEURODEGENERATIVE DISEASES

(75) Inventors: Lee Laurence Rubin, London; Susan Frances Brooks, deceased, late of St. Albans, both of (GB), Gavin Brooks, executor

(73) Assignee: Eisai Co., Ltd., Tokyo (JP)

( * ) Notice: Under 35 U.S.C. 154(b), the term of this patent shall be extended for 0 days.

This patent is subject to a terminal disclaimer.

(21) Appl. No.: 09/137,449

(22) Filed: Aug. 14, 1998

Related U.S. Application Data

(63) Continuation of application No. 08/556,974, filed as application No. PCT/GB94/01169 on May 31, 1994, now Pat. No. 5,840,719.

(30) Foreign Application Priority Data

May 28, 1993 (GB) .................................................. 9311132

(51) Int. Cl.[7] ........................ A61K 31/405; A61K 31/34; A61K 31/135; A61K 31/56; A61K 31/505; A61K 31/52; A61K 31/47; A61K 31/44

(52) U.S. Cl. .......................... 514/180; 514/181; 514/258; 514/261; 514/263; 514/275; 514/309; 514/334; 514/415; 514/474; 514/646

(58) Field of Search .................................... 514/180, 181, 514/258, 261, 263, 275, 309, 334, 415, 474, 646

(56) References Cited

U.S. PATENT DOCUMENTS 5,840,719 * 11/1998 Rubin et al. .................. 514/180

FOREIGN PATENT DOCUMENTS 0552373 7/1993 (EP) .

92/17193 10/1992 (WO) .

OTHER PUBLICATIONS

Finnegan, et al., Role For Protein Synthesis in the Neurotoxic Effects of Methaphetamine in Mice and Rats; (1992) Brain Research, vol. 591: pp. 160–164.

Rukenstein, et al., Multiple Agents Rescue PC12 Cells from Serum–free Cell Death by Translation– and Transcription–independent Mechanisms; (1991) The Journal of Neuroscience, vol. 11(8); pp. 2552–2563.

Ferrari, et al., Gangliosides Rescue Neuronal Cells from Death after Tropic Factor Deprivation; (1993) The Journal of Neuroscience, vol. 13(5); pp. 1879–1887.

Batistatou, et al., Aurintricarboxylic Acid Rescues PC12 Cells and Sympathetic Neurons from Cell Death Caused by Nerve Growth Factor Deprivation: Correlation with Suppression Endonuclease Activity; (1991) J. Cell Biol., vol. 115(2); pp. 461–472.

Galli, et al., Activation of Apoptosis by Serum Deprivation in a Teratocarcinoma Cell Line: Inhibition by L–Acetylcarnitine; (1993) Experimental Cell Research, vol. 204; pp. 54–60.

Davidoff, et al., Substituted Purines Elicit Differential Cytokinetic, Molecular and Phenotypic Effects in HL–60 Cells, (1993) Experimental Hematology, vol. 21; pp. 456–460.

Thakkar, et al., Abrogation of Adriamycin Toxicity in Vivo by Cycloheximide; (1992) Biochemical Pharmacology, vol. 43(3); pp. 1683–1691.

* cited by examiner

Primary Examiner—Kimberly Jordan
(74) Attorney, Agent, or Firm—Hale and Dorr LLP

(57) ABSTRACT

Apoptotic cell death in a fully differentiated, non-dividing cell such as a neuron is caused by an abortive attempt of the cell to re-enter or pass through the mitotic cycle. Therefore, agents which prevent such entry or passage are effective in preventing, or at least delaying, apoptotic cell death and are therefore useful in the treatment of neurodegenerative diseases in general, including stroke, Alzheimer's disease, Parkinson's disease and motor-neuron disease in particular.

22 Claims, 11 Drawing Sheets

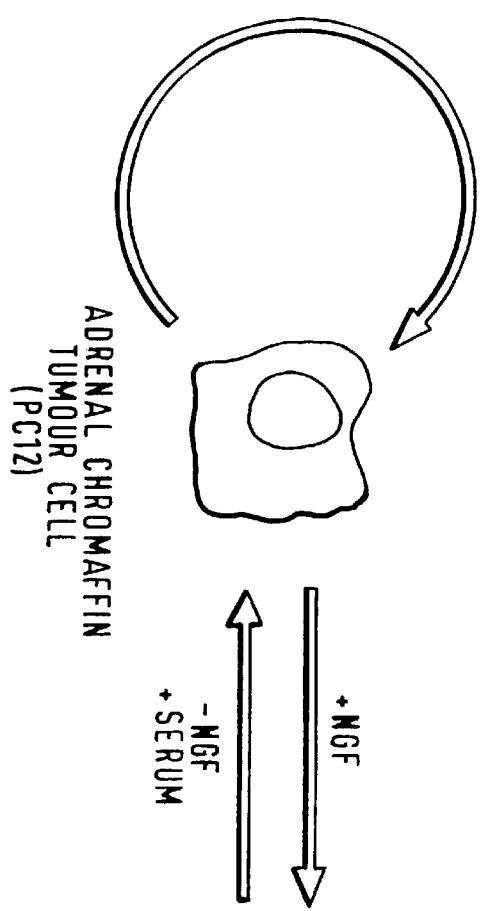
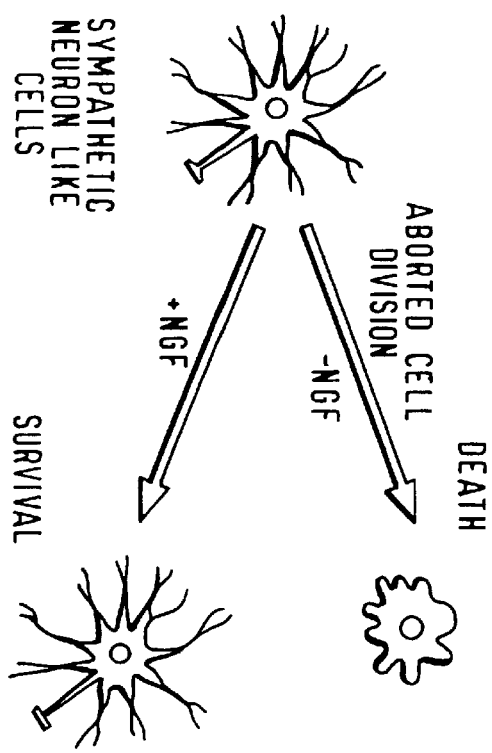
FIG. 1

TIME (HOURS) AFTER NGF WITHDRAWAL

SEROTONIN (MW = 387.4)

Dopamine (MW = 189.6)

Hydrocortisone (MW =362.5)

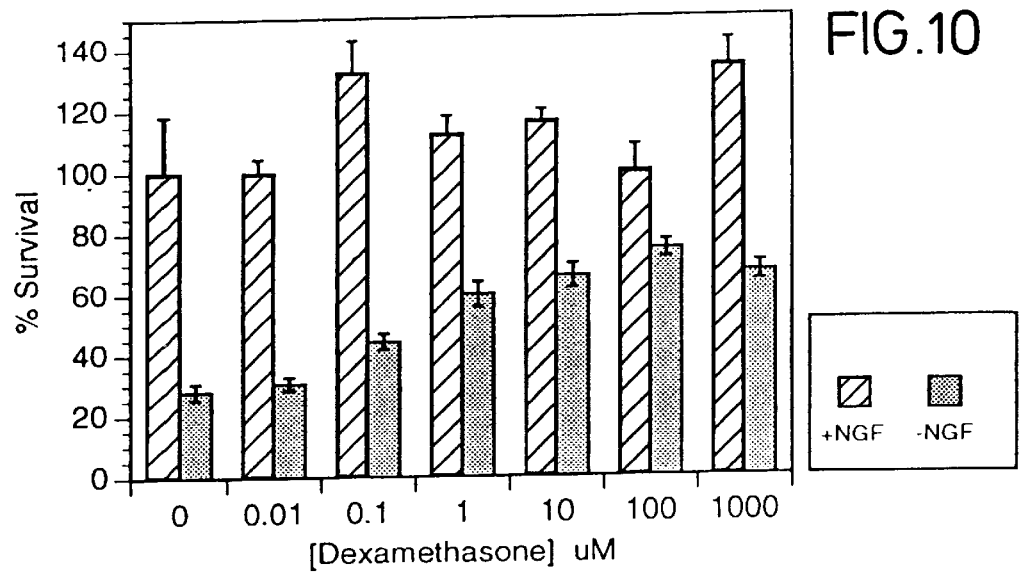
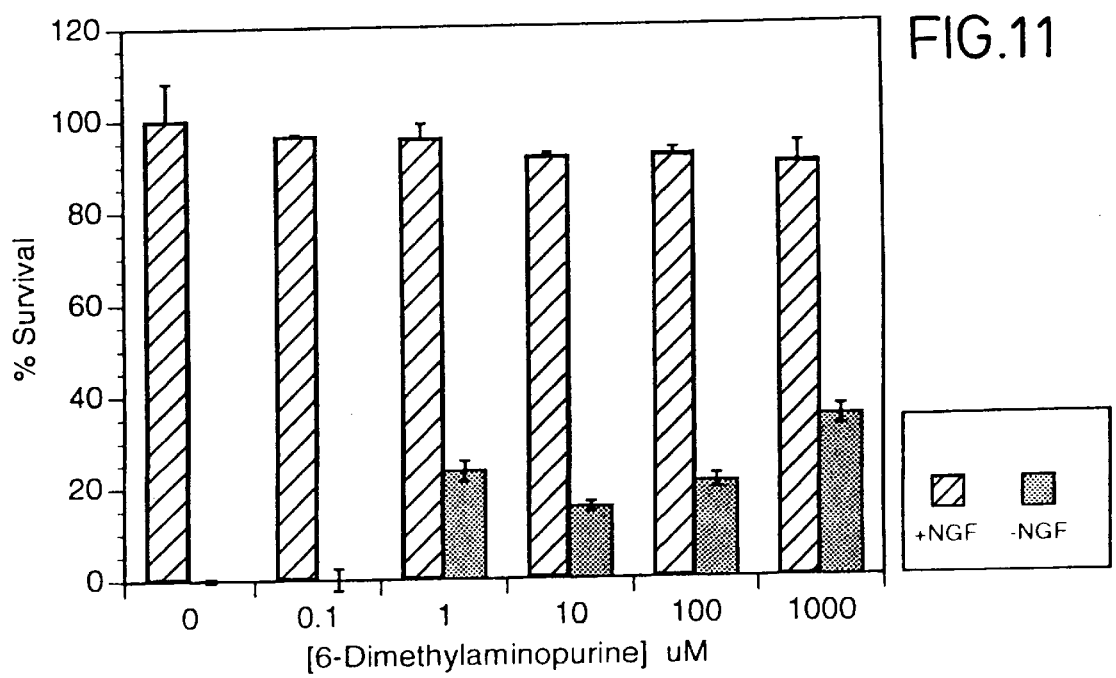

**Effect of bcl-2 overexpression on activation of cdc2
induced by staurosporine in quiescent rat1 fibroblasts**

APOPTOSIS INHIBITORS FOR TREATING NEURODEGENERATIVE DISEASES

This application is a continuation of Ser. No. 08/556,974, filed May 8, 1996, now U.S. Pat. No. 5,840,719, which is a 371 of PCT/GB94/01169, filed May 31, 1994.

This invention relates to the prevention or at least delay of death of cells, particularly non-dividing cells.

Controlling cell death is useful in the treatment of neurodegenerative diseases in general, including stroke, Alzheimer's disease, Parkinson's disease and motor-neuron disease in particular.

Neurons are examples of cells which have terminally differentiated and therefore are non-dividing. There are two general types of neuronal cell death: necrotic and apoptotic. The two differ in terms of initiating factors, morphological changes, time course and mechanism. Necrotic cell death is often seen in situations in which there is excess calcium ion influx caused, for example, by application of the excitatory neurotransmitter glutamate. Apoptotic cell death is sometimes referred to as programmed cell death and is seen as a normal developmental event in the nervous system and in other tissues. Fully differentiated neurons are normally dependent on a trophic factor for their survival and apoptotic death can be triggered by trophic factor withdrawal.

The role of apoptotic death in neurodegenerative disease has not been fully established. However, there are a variety of diseases of the nervous system in which neurons destined to die can be rescued by application of appropriate growth factors. While the cause of a cell's fate may vary from disease to disease, it seems likely that the final death pathway is apoptosis in each case.

The observation that the application of appropriate growth factors can rescue neurons destined to die has given rise to proposals for treatment for certain neurodegenerative diseases in the past. However, because the treatment is based on the use of peptide growth factors, which are unable to cross the blood-brain barrier, most current clinical trials for neurodegenerative disease are for diseases of the peripheral, rather than central, nervous system. Furthermore, such individual treatments as have been proposed are rather disease-specific; there has not hitherto existed the basis for developing a more generally applicable therapeutic or prophylactic regime for the management of neurodegenerative disease and other diseases involving the cell death of non-dividing cells.

It has now been discovered that cell death in a fully differentiated, non-dividing cell such as a neuron appears to be the result of an abortive attempt of the cell to re-enter or pass through the mitotic cycle. Therefore, agents which prevent entry into or passage through the mitotic cycle should be effective in preventing, or at least delaying, apoptotic cell death.

According to a first aspect of the present invention, there is provided a method of treating or preventing a disease involving apoptotic cell death, the method comprising administering to a subject, or to cells of a subject, an effective amount of an agent which prevents cell entry into or passage through the mitotic cycle; provided that the agent is not bFGF, IGF-I, IGF-II, potassium ions or a cAMP-elevating agent.

The mitotic cell cycle has four distinct phases, $G_1$, S, $G_2$ and M. The beginning event in the cell cycle, called start, takes place in the $G_1$ phase and has a unique function. The decision or commitment to undergo another cell cycle is made at start. Once a cell has passed through start, it passes through the remainder of the $G_1$ phase, which is the pre-DNA synthesis phase. The second stage, the S phase, is when DNA synthesis takes place. This is followed by the $G_2$ phase, which is the period between DNA synthesis and mitosis. Mitosis itself occurs at the M phase. Fully differentiated cells such as neurons are generally regarded as not being in any of these four phases of the cycle; they are usually described as being in a $G_0$ state, so as to indicate that they would not normally progress through the cycle.

Preferred agents useful in the invention may totally prevent entry into the cycle. Other agents may allow passage through the cycle to a certain extend but not completely. In some cases it well be preferred to block passage through the cycle relatively early on; in other cases, blocking later may be more appropriate. Generally, agents may block the cycle at $G_1$, $G_1$/S, S or S/$G_2$.

Agents which may totally prevent entry into the cycle may include FK-506.

Agents which block the cell cycle at the $G_1$ phase include agents which interfere with early gene expression or which interfere with the proper functioning of the products of early expressed genes. Examples of early expressed genes include c-fos, c-jun and c-myc. Agents which prevent the phosphorylation state of the retinoblastoma (Rb) protein may also block the cycle at this early stage.

The cell cycle may be stopped at the late $G_1$ stage by agents which interfere with the expression or proper functioning of cyclin D or E. (Interference, in this and other cases, may be direct or indirect). Correspondingly, the cell cycle may be stopped at the $G_1$/S stage by agents which interfere with the expression or proper functioning of cyclin A and/or D. Other agents which block the cell cycle at $G_1$/S include those which interfere (directly or indirectly) with the activation of the enzymes cdc2, cdk2 and/or cdk4; the activated form of cdk2 has been shown to be necessary for normal passage through the S phase.

The principal way of preventing passage through the S phase is of course to block DNA synthesis. Many agents useful for this purpose, including the use of nucleotide analogues such as dideoxynucleotides and the use of inhibitors of DNA polymerase, are known in the art.

Among agents useful in blocking the cell cycle at the $G_2$ phase are those which inhibit, directly or indirectly, inactivation of the enzymes cdc2 and cdk2.

The cell cycle may be stopped at $G_2$/M stage by agents which interfere with the expression or proper functioning of cyclin G and/or those which inhibit the reactivation of the enzyme cdc2.

Finally, the cycle may be stopped at the M phase by interfering with the proper processing and organisation of tubulin.

Generally speaking, it is possible to monitor the stage in the mitotic cycle at which the passage of cells have been stopped by looking for the expression, proper functioning, activation or inhibition, as the case may be, of the various genes and enzymes discussed above. In addition, in the S phase, the extent of DNA synthesis taking place can be assessed by any suitable method such as might be used for assessing DNA synthesis in other situations. Examples include measuring the incorporation of a detectable nucleotide, such as bromodeoxyuridine (BrdU), and fluorescence-activated cell sorting (FACS) analysis based on the intercalation of a suitable fluorescent dye, such as propidium iodide. In fact, not only does the extent of DNA synthesis serve as a marker of whether cells are in the S or subsequent phases of the mitotic cell cycle (in which case the cells have a double DNA complement), it also serves as a marker of whether cells are undergoing cell death (in which case the DNA complement of the cells is less than the normal, single level). An additional marker of cells being in the M phase is provided by the gross morphological changes (including chromosome condensation and nuclear envelope breakdown) which are taking place then.

To summarise, there are a number of different ways in which agents useful in the invention may prevent entry into the mitotic cell cycle. First, DNA synthesis could be inhibited. Secondly, cell division cycle-associated enzymes could be inhibited. Many of these enzymes are encoded by the cdc series of genes; additionally, many of the enzymes involved are kinases or phosphatases. Either the enzyme itself may be inhibited, or its activation, from a precursor, could be inhibited. Equally, entry into the mitotic cycle can be measured in a number of different ways. Markers of DNA synthesis can be used; or other cell cycle markers can be examined. Such cell cycle markers include cyclin synthesis, cdc2 or cdk2 activation, early gene expression and redistribution or modification of certain transcription factors.

Broadly speaking, compounds can be assessed for their potential usefulness in the invention by their ability to inhibit in vitro, as a model for their activity in vivo, any of the processes of the cell cycle described above. Enzyme inhibition assays, based on the enzymes involved in the cycle, can therefore act as screens for useful compounds.

One particular way of assessing candidate compounds for their usefulness of the invention is to use the following model. PC12 rat pheochromocytoma cells are adrenal chromaffin-like cells which have the ability to differentiate terminally into a sympathetic neuron-like phenotype in response to nerve growth factor (NGF). If these differentiated cells are subsequently withdrawn from NGF, they undergo a series of morphological and biochemical changes that are characteristic of cell death by apoptosis. Compounds can be screened by assessing their ability to prevent PC12 cell death following NGF withdrawal. FIG. 1 of the accompanying drawings shows the life and death of a PC12 cell. In the presence of serum alone, these cells will divide and survive. In the presence of NGF or NGF plus serum, they will differentiate and survive. But in the absence of NGF and serum, the cells die unless a compound useful in the invention is present).

In principle, any agent which prevents cell entry into or passage through the mitotic cycle could be useful in the invention. Practical considerations dictate that compounds useful in the invention will have a sufficiently low toxicity to result in a useful therapeutic index. Preferred compounds useful in the invention will be those which are readily formulatable and pharmaceutically (or veterinarily) acceptable formulations; however, continuing advances in formulation technology are likely to result in a few, if any, real limitations in this respect. Preferred compounds useful in the invention as able to cross the blood-brain barrier, as they would then be useful in preventing cell death in neurons of the central nervous system. Even if compounds cannot cross the blood-brain barrier, though, they may still be useful in the invention in preventing cell death in neurons of the peripheral nervous system and other, non-neuronal, cell types.

One particular cell-associated kinase whose activation may usefully be inhibited in the practice of the present invention is $p34^{cdc2}$. Inhibitors of the activation of $p34^{cdc2}$ kinase include 6-dimethylaminopurine (6-DMAP); analogues of 6-DMAP and other compounds may also be used in the invention.

FIG. 2 of the accompanying drawings shows a hypothetical framework showing the complexity of potential interactions among various cell cycle elements during neuronal apoptosis initiated by NGF withdrawal in a model system. This scheme is based on a situation in which cdc2 kinase is activated in the absence of NGF and leads to neuronal apoptosis, perhaps by modification of structural elements such as the nuclear envelope. Partly as a result of this complexity, a large number of approaches to selecting compounds useful in the invention becomes apparent. cdc2 is normally phosphorylated and inactivated by wee1 and mik1 kinases and activated by cdc25 phosphatase. It also requires an associated regulatory subunit, such as the $G_2/M$ cyclin B for activity. c-mos is included as a potential regulatory factor that interacts with cyclic AMP via protein kinase A (PKA) and $Ca^{2+}$, known to be neuronal survival agents. So, just considering classes of compounds useful in the invention as a result of their interference with the normal functioning of cdc2, it can be seen that the following, among others, are useful:

promoters or activators of wee1 and/or mik1;

inhibitors of cdc25; and/or antagonists of cyclin B.

Among the specific compounds that have been shown to be capable of preventing cell death are serotonin (>10 mM), dopamine (>10 mM), ascorbin acid (>100 mM), gluquidone (>10 mM), caffeine (>1 mM) and high doses of the steroids hydrocortisone (0.1 to 100 μM) and dexamethasone (>0.1 mM).

The use of bFGF, insulin-like growth factors I and II (IGF-I and IGF-II), depolarisation with potassium ions and certain cAMP elevating agents including certain cAMP-analogues is excluded from the invention as defined herein because these specific agents have previously been shown to prevent neuronal cell death. For example: bFGF has been shown to support the survival of cerebral cortical neurons in primary culture by Morrison et al. (*Proc. Nat'l. Acad. Sci. USA* 83 7537–7541 (1986)); IGF-I and IGF-II have been shown to rescue PC12 cells from serum-free death by Rukenstein et al. (*J. Neurosci.* 11 2552–2563 (1991)); high $K^+$ concentrations have been shown to support the survival of chick embryo sympathetic neurons by Wadake et al. (*Exp. Cell. Res.* 144 377–384 (1983)); and the following cAMP elevating agents have been shown to prevent cell death:

8-(4-chlorophenylthio)-adenosine-3':5'-cyclic-menophosphate (CPT-cAMP) (see, for example, Koike *Prog. Neuro-Psychopharmacol. and Biol. Psychiat.* 16 95–106 (1992)), CPT-cAMP, forskolin, isobutyl methylxanthine (IBMX) and cholera toxin (see Martin et al. *J. Neurobiol.* 23 1205–1220 (1992)) and 8-bromo-cAMP, $N^6,O^{2'}$-dibutyryl-cAMP and $N^6,O^{2'}$-dioctanoyl-cAMP (see Rydel and Greene *Proc. Nat'l. Acad. Sci. USA* 85 1257–1261 (1988)).

However, it was not until the present invention was made that the mode of action of the above compounds, as an apparently unrelated group of structurally and functionally diverse compounds, could satisfactorily be explained by a unified theory. There was therefore no motivation, before this invention, to seek other agents which also prevent cell entry into, or successful passage through, the mitotic cycle.

The invention is in general useful in preventing cell death in all non-dividing cells. Examples include muscle cells (such as striated muscle cells and heart myocytes (Nazareth et al. *J. Mol. Cell. Cardiol.* 23 1351–1354 (1991)) and neurons.

While the invention has particular application in the treatment and prophylaxis of disease in humans, there is no reason in principle why it should not be applied to animals of other species.

Compounds useful in the invention may, depending on their physical and chemical properties, be administered on their own but will generally be formulated with a pharmaceutically or veterinarily acceptable carrier. The preferred mode of long term treatment of degenerative disease, particularly neurodegenerative disease, is to use agents that are bioactive and bioavailable when administered enterally (particularly orally), so orally administrable formulations are of particular importance. If a neurodegenerative disease of the central nervous system is to be treated by means of an oral formulation, the agent should additionally be able to cross the blood-brain barrier. Agents which cannot cross the blood-brain barrier, such as certain peptides and polypeptides, are not necessarily precluded from being useful in the invention, even in the treatment of neurodegenerative disease, as they may be administered locally, for example by the use of an Omaya reservoir or, in the case of peptides and polypeptides, by the implantation of appropriate cells expressing and secreting the factor.

The dosage of any particular agent will depend on a number of factors and is likely to be optimised in experimental or clinical trials. In any event, the appropriate dosage for a particular patient or subject will be determined by the responsible physician or clinician in each case.

The invention extends to the use of an agent (other than bFGF, IGF-I, IGF-II, potassium ions or a cAMP-elevating agent) which prevents cell entry into, or passage through, the mitotic cycle in the preparation of a medicament for treating or preventing a disease involving apoptotic cell death.

Diseases treatable by means of the invention include neurodegenerative diseases in general, including stroke, Alzheimer's disease, Parkinson's disease and motor-neuron disease in particular.

The invention may also have application in non-medical fields. According to a second aspect of the invention, there is provided a method of preventing apoptotic cell death, the method comprising administering to cells an effective amount of an agent which prevents cell entry into the mitotic cycle, provided that the agent is not bFGF, IGF-I or IGF-II, potassium ions or a cAMP-elevating agent.

Such a method may be useful in laboratory modelling studies, possibly in research on the aetiology of cell death.

Preferred features of the second aspect of the invention are as for the first aspect, mutatis mutandis.

BRIEF DESCRIPTION OF THE DRAWINGS

The invention will now be illustrated by the following examples. The examples refer to the drawings, in which:

FIG. 1 shows schematically the life and death of a PC12 cell;

FIG. 10 relates to Example 9 and is a bar chart showing that dexamethasone promotes cell survival in conditions leading to apoptosis;

FIG. 11 relates to Example 10 and is a bar chart showing that 5-dimethylaminopurine promotes cell survival in conditions leading to apoptosis;

PREPARATION

Maintenance and Differentiation of PC12 Cells

PC12 rat pheochromocytoma cells (Greene and Tischler *Proc. Nat'l. Acad. Sci. USA* 73 2424–2428 (1976)), obtained from Dr. P. Doherty, Department of Experimental Pathology, United Medical and Dental School, Guy's Hospital, London Bridge, London SE1 9RT, where maintained in an undifferentiated state by seeding at a density of $8 \times 10^4$ cells/cm$^2$ onto a collagen substrate in SATO medium containing 2% heat-inactivated foetal calf serum (GIBCO) and 10 mg/l insulin (Sigma) in a humidified atmosphere at 37° C. in 8% $CO_2$. Cells were re-fed every 3–4 days. (SATO medium is Dulbecco's Modified Eagles' Medium (DMEM) containing:

4.32 g/l BSA (Pathocyte 4; ICN),
0.075 mg/l progesterone (Sigma),
20.0 mg/l putrescine (Sigma),
0.5 mg/l L-thyroxine (Sigma),
0.05 mg/l selenium (Sigma),
0.4175 mg/l tri-iodo-thyronine (Sigma),
125 mg/l transferrin (Sigma) and
1.25 mM glutamine (GIBCO).)

PC12 cells were differentiated by passaging into serum- and insulin-free SATO medium containing 100 ng/ml nerve growth factor (NGF) (purified from male submaxillary glands as described (Winter et al. *Neuron* 1 973–981 (1988) and Suda et al. *Proc. Nat'l. Acad. Sci. USA* 75 4042–4046 (1978)). Cells were plated onto polylysine-( 16 μg/ml) and collagen-coated dishes at a density of $8 \times 10^4$ cells/cm$^2$ and were maintained in a humidified atmosphere at 37° C., 8% $CO_2$, for 7 days. Cells were re-fed every 3 days.

EXAMPLE 1

Cells Undergoing Apoptosis Activate p34$^{cdc2}$, a Kinase Specific to the Cell Division Cycle PC12 cells were plated onto polylysine/collagen-coated 90 mm plates at a density of $2 \times 10^6$ cells/dish, and were allowed to differentiate for 7 days as in the Preparation.

Figure 2:
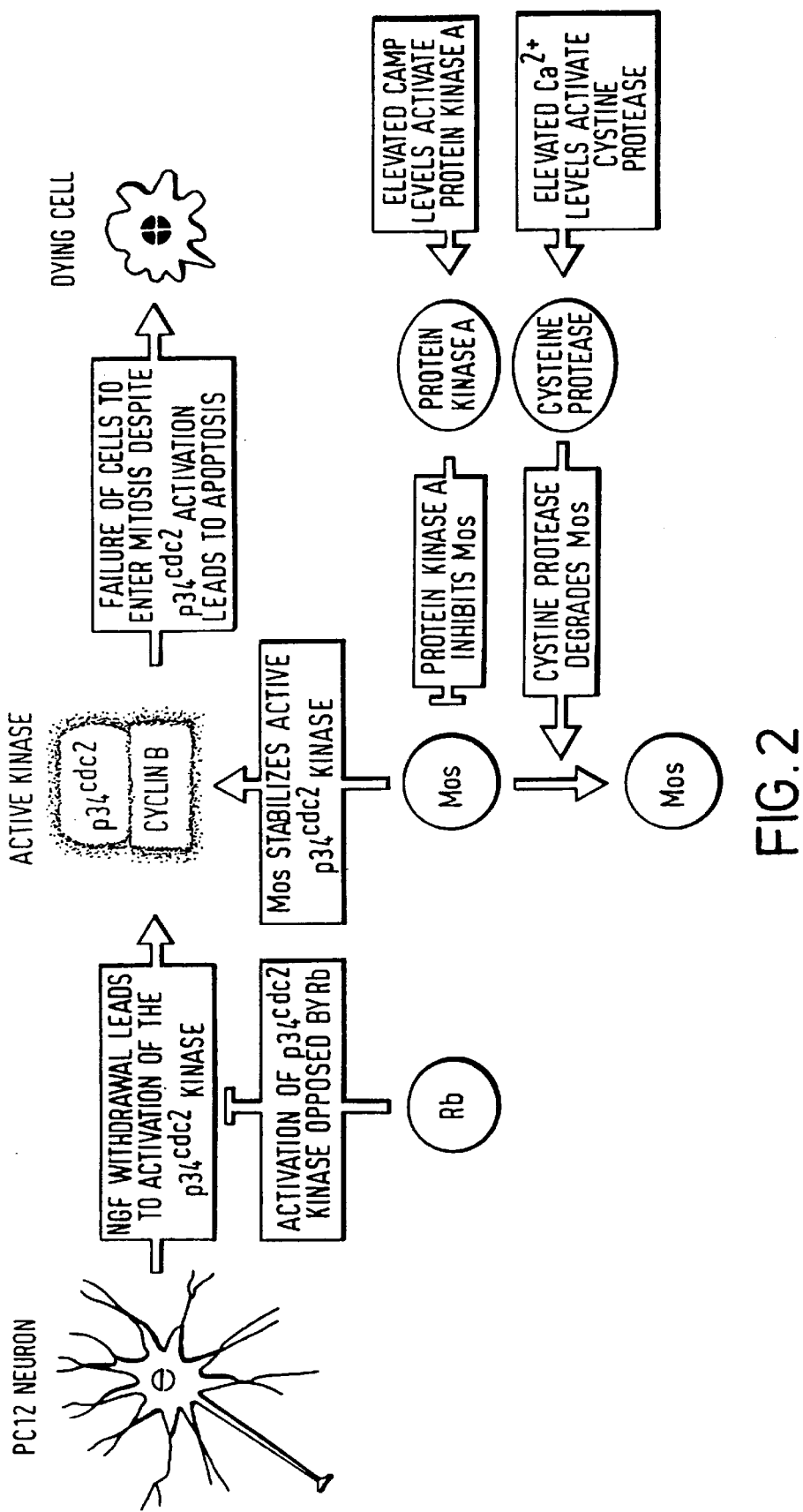
FIG. 2 shows a hypothetical framework showing the complexity of potential interactions among various cell cycle elements during neuronal apoptosis initiated by NGF withdrawal.
Figure 3:
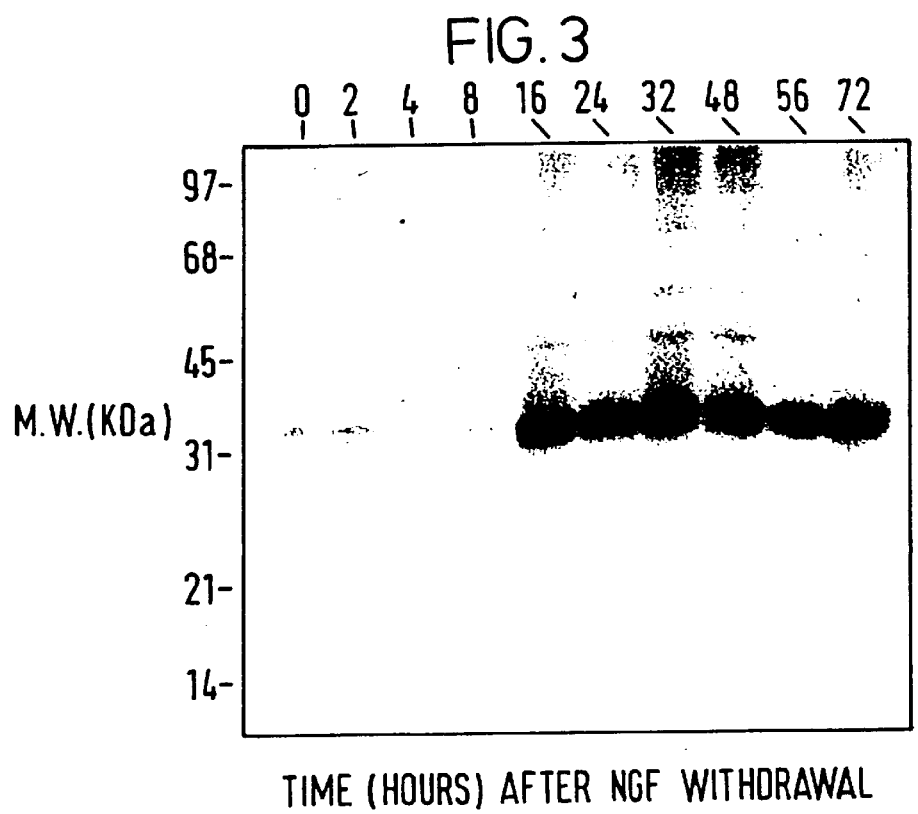
FIG. 3 relates to Example 2 and is an autoradiograph of a 12.5% SDS-polyacrylamide gel showing that $p34^{cdc2}$ kinase is activated in conditions leading to apoptosis.

After washing twice with DMEM cells were incubated in SATO medium containing anti-NGF antibody for various periods of time. Medium was removed from the cells, and any floating cells were pelleted by centrifugation at 1000 rpm for 10 min. Adherent cells were washed once with PBS at 4° C., and then lysed in 0.5 ml ice cold lysis buffer (50 mM Tris/HCl pH 7.4, 0.25M NaCl, 0.1% NP-40, 5 mM EDTA, 50 mM NaF, 1 mM sodium orthovanadate, 1 mM sodium pyrophosphate, 50 μg/ml PMSF, 10 μg/ml TPCK, 10 μg/ml soy bean trypsin inhibitor, 1 Mg/ml aprotinin, 1 μg/ml leupeptin). An aliquot of the lysate was used to resuspend the cells pelleted by centrifugation, and was then combined with the lysate from the adherent cells. After 30 min incubation on ice, the suspension was centrifuged at 13,000 g for 5 min at 4° C., and the supernatant containing cdc2 kinase was collected. Samples were adjusted to a final volume of 750 μl containing equal protein, and were then pre-cleared with 40 μl protein A-SEPHAROSE beads (Boehringer Mannheim) by incubation on a rotating wheel at 4° C. for 1 h. The beads were then removed by centrifugation for 15 s at 13,000 g, and the supernatant was then incubated with 1:100 dilution of anti-cdc2 antibody for 2 h at 4° C. (The anti-cdc2 antibody was raised in rabbits to a peptide containing the eight C-terminal amino acids of the human cdc2 protein ($NH_2$-CGGLDNQIKKM-COOH) and was a gift from Dr. C. Barth, Imperial Cancer Research Fund, Lincoln's Inn Fields, London WC2A 3PX.) The cdc-2/antibody complex was then bound to protein A-SEPHAROSE beads by incubation for 40 μl beads for 1 h at 4° C. The complex was then pelleted by centrifugation for 15 s at 13,000 g. After washing 4 times in 1 ml lysis buffer, the pellet was washed once in PKA wash buffer (50 mM Tris/HCl pH 7.4, 10 mM $MgCl_2$, 1 mM DTT), and then resuspended in 25 μl of the same buffer containing 125 μg/ml histone H1. After 2 min incubation at 30° C., the reaction was initiated by the addition of 5 μl ATP mix (1 μM ATP, 10 μCi/μl [γ-$^{32}$P]ATP in PKA wash buffer), and samples were incubated at 30° C. for 10 min. The reaction was terminated by the addition of an equal volume of 2xLaemmli sample buffer and by incubating for 3 minutes at 100° C. Samples were separated on a 12.5% SDS polyacrylamide gel. After drying, the gel was exposed to X-ray film, and kinase activity was assessed by the extend of incorporation of $^{32}$P into histone H1. The results are shown in FIG. 3. Phosphorylated histone H1 can be visualised as a doublet migrating at ~35 kDa some 16 hours after NGF withdrawal.

EXAMPLE 2

Serotonin Promotes Cell Survival Under Conditions Leading to Apoptosis

Figure 4:
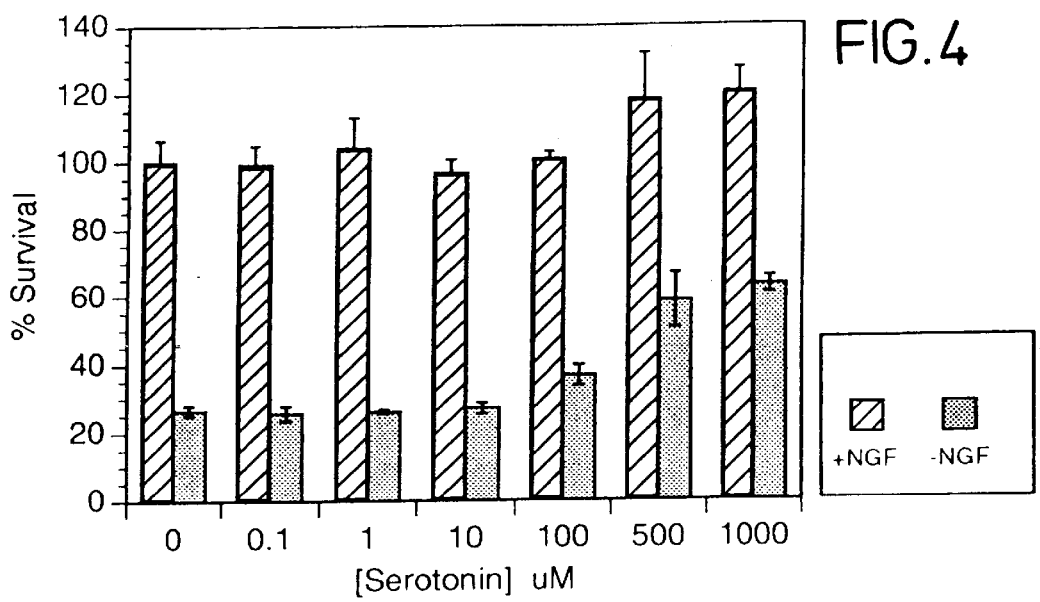
FIG. 4 relates to Example 3 and is a bar chart showing that serotonin promotes cell survival in conditions leading to apoptosis.

PC12 cells were plated onto polylysine/collagen-coated 96 well microtitre plates at a density of $7.5 \times 10^3$/well and were allowed to differentiate for 7 days in SATO medium containing 100 ng/ml NGF. After washing one with DMEM, cells were incubated in SATO medium containing 62.5 ng/ml anti-NGF antibody Boehringer Mannheim) and various concentrations of serotonin for various periods of time. Viability was then measured by the ability of cells to take up and metabolise the yellow dye MTT to the dark blue compound MTT-formazan. This product was then detected spectrophotometrically. The results are shown in FIG. 4.

EXAMPLE 3

Dopamine Promotes Cell Survival in Conditions leading to Apoptosis

Figure 5:
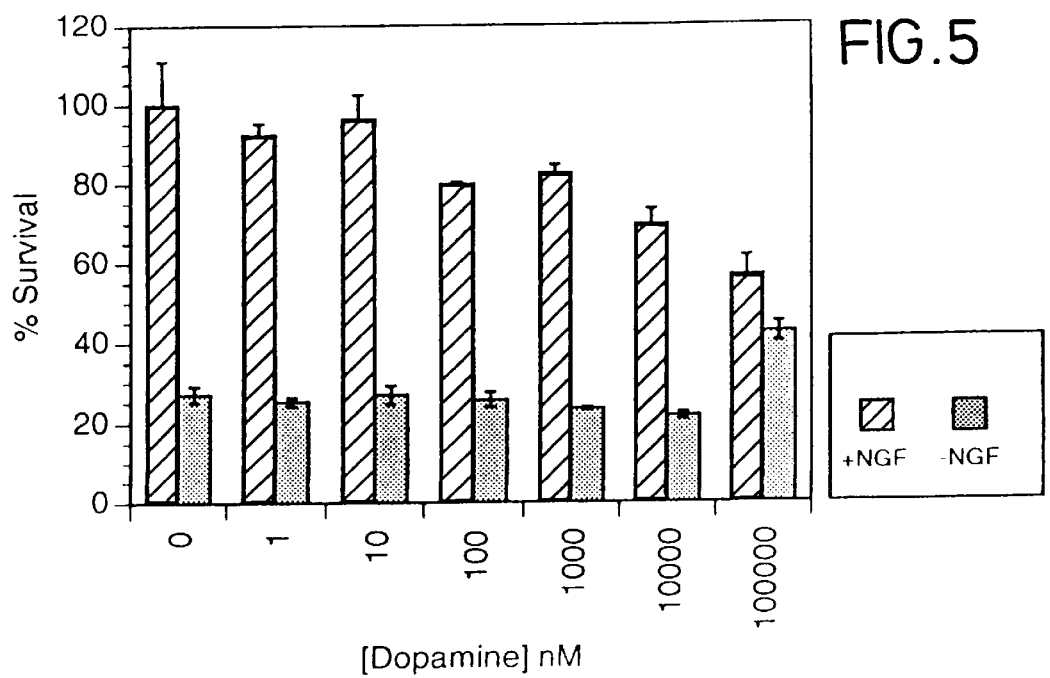
FIG. 5 relates to Example 4 and is a bar chart showing that dopamine promotes cell survival in conditions leading to apoptosis.

The experiment of Example 2 was repeated, except that various concentrations of dopamine were used in place of serotonin. The results are shown in FIG. 5.

EXAMPLE 4

L-Ascorbin Acid Promotes Cell Survival in Conditions leading to Apoptosis

Figure 6:
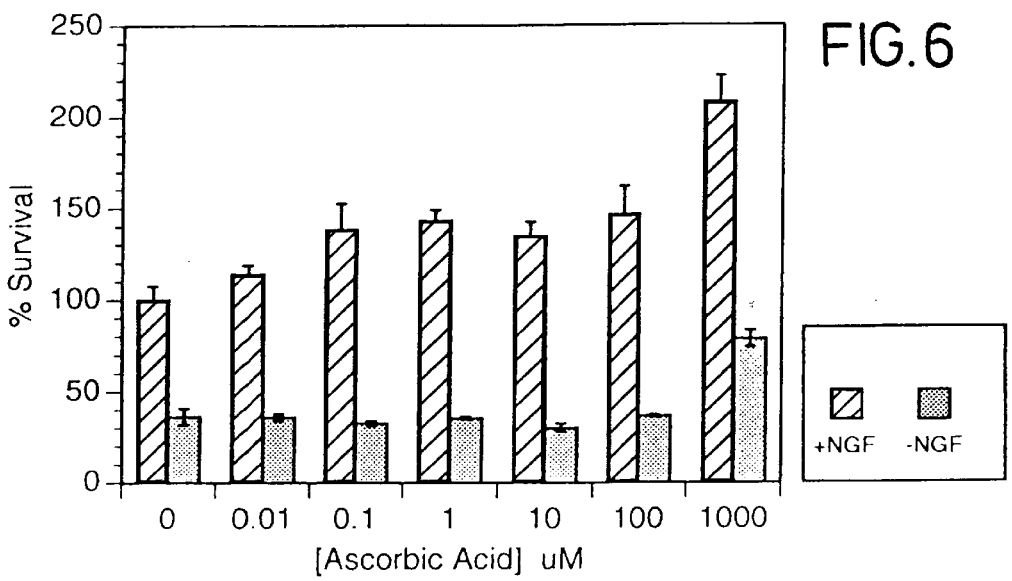
FIG. 6 relates to Example 5 and is a bar chart showing that L-ascorbic acid promotes cell survival in conditions leading to apoptosis.

The experiment of Example 2 was repeated, except that various concentrations of L-ascorbic acid were used in place of serotonin. The results are shown in FIG. 6.

EXAMPLE 5

Gliquidone Promotes Cell Survival in Conditions leading to Apoptosis

Figure 7:
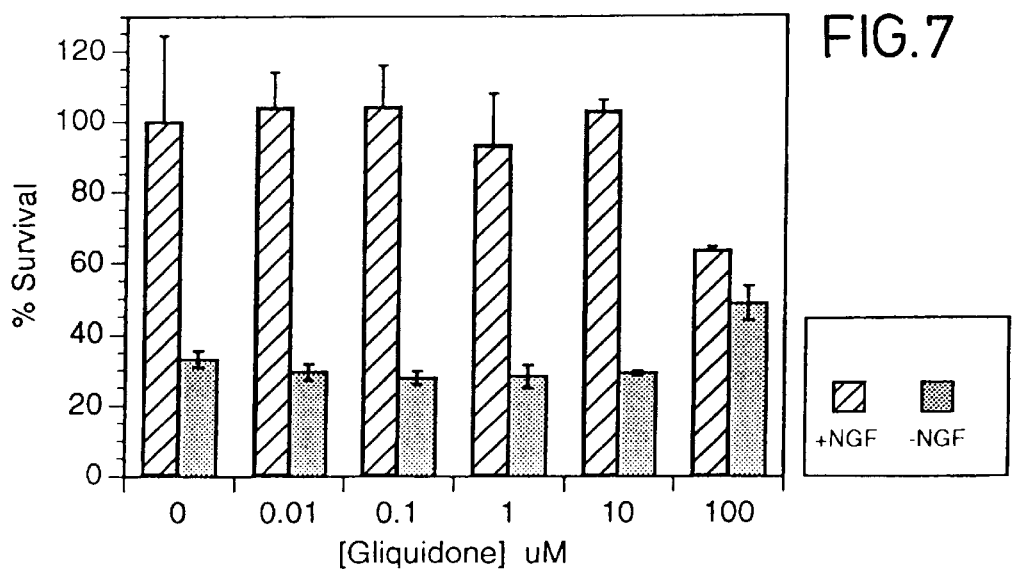
FIG. 7 relates to Example 6 and is a bar chart showing that gliquidone promotes cell survival in conditions leading to apoptosis.

The experiment of Example 2 was repeated, except that various concentrations of gliquidone were used in place of serotonin. The results are shown in FIG. 7.

EXAMPLE 6

Caffeine Promotes Cell Survival in Conditions leading to Apoptosis

Figure 8:
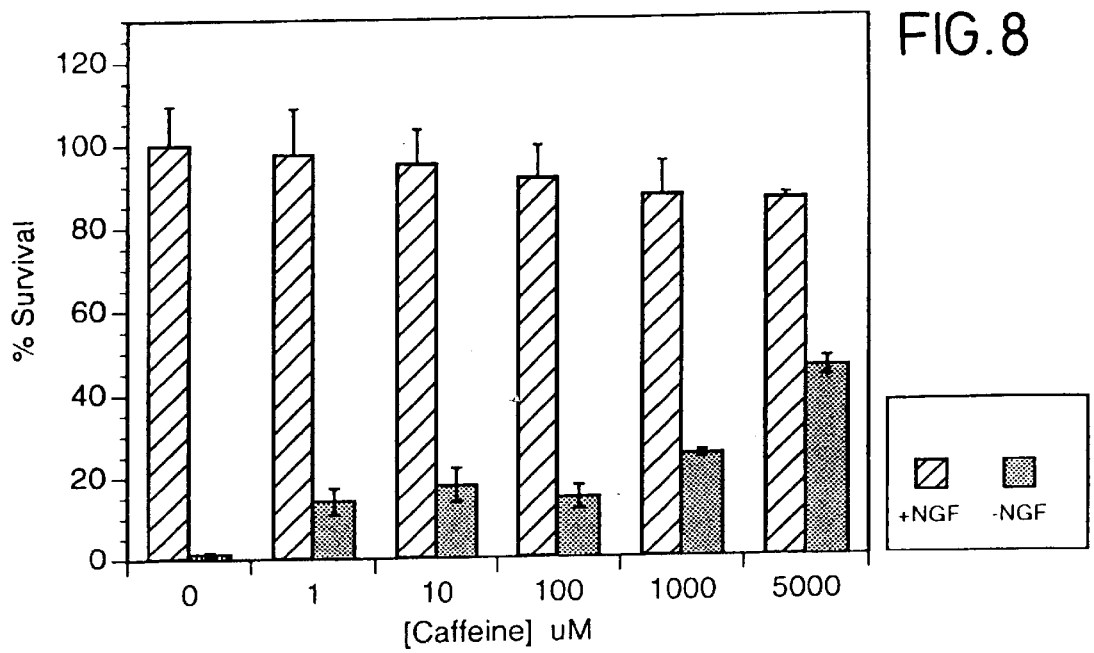
FIG. 8 relates to Example 7 and is a bar chart showing that caffeine promotes cell survival in conditions leading to apoptosis.

The experiment of Example 2 was repeated, except that various concentrations of caffeine were used in place of serotonin. The results are shown in FIG. 8.

EXAMPLE 7

Hydrocortisone Promotes Cell Survival in Conditions leading to Apoptosis

Figure 9:
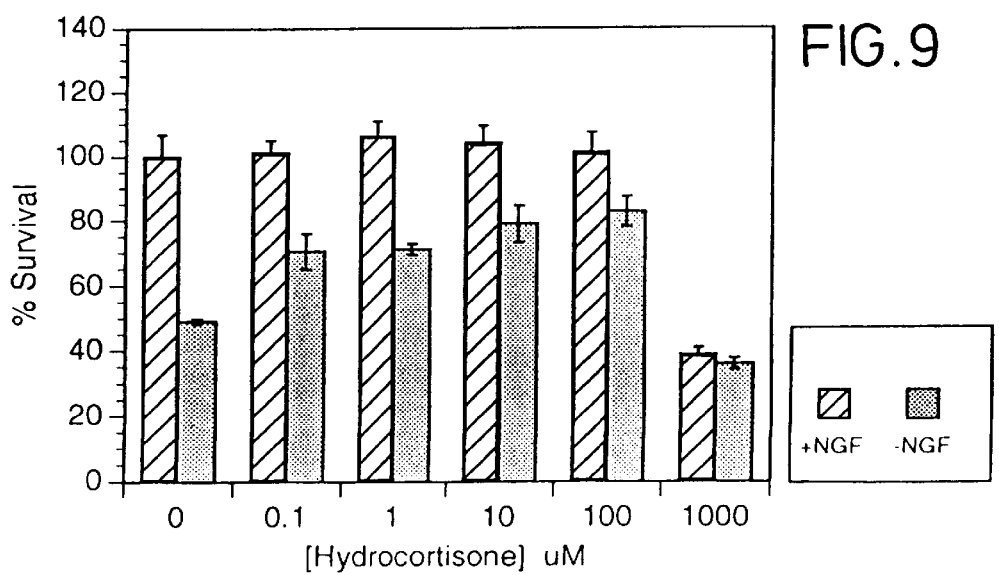
FIG. 9 relates to Example 8 and is a bar chart showing that hydrocortisone promotes cell survival in conditions leading to apoptosis.

The experiment of Example 2 was repeated, except that various concentrations of hydrocortisone were used in place of serotonin. The results are shown in FIG. 9.

EXAMPLE 8

Dexamethasone Promotes Cell Survival in Conditions leading to Apoptosis

The experiment of Example 2 was repeated, except that various concentration of examethasone were used in place of serotonin. The results are shown in FIG. 10.

EXAMPLE 9

6-Dimethylaminopurine Promotes Cell Survival in Conditions leading to Apoptosis

The experiment of Example 2 was repeated, except that various concentrations of 6-dimethylaminopurine (6-DMAP) were used in place of serotonin. The results are shown in FIG. 11.

EXAMPLE 10

Dipyridamole Promotes Cell Survival in Conditions leading to Apoptosis

Figure 12:
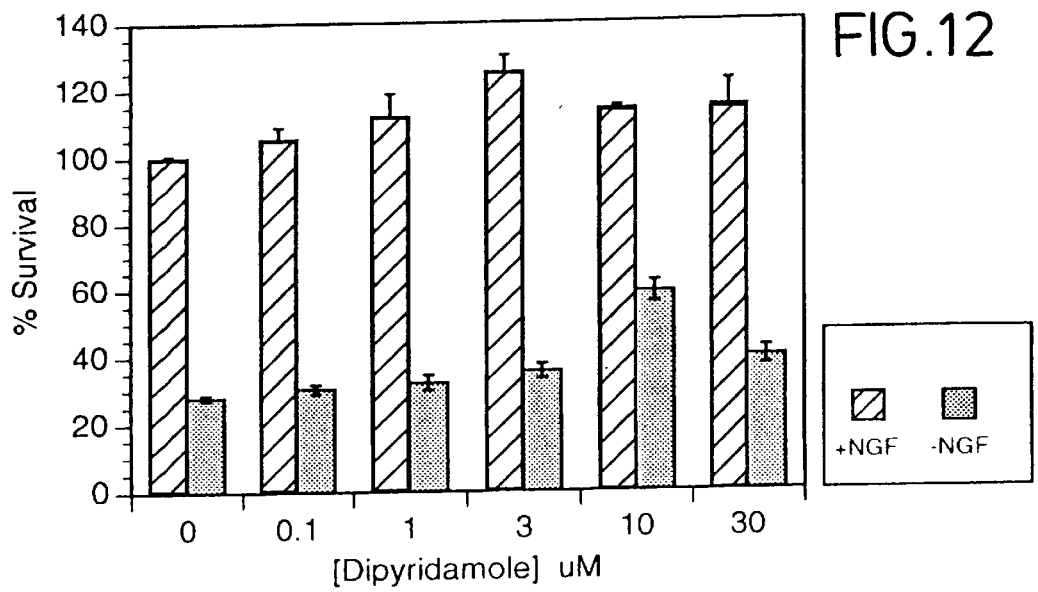
FIG. 12 relates to Example 11 and is a bar chart showing that dipyridamole promotes cell survival in conditions leading to apoptosis.

The experiment of Example 2 was repeated, except that various concentrations of dipyridamole were used in place of serotonin. The results are shown in FIG. 12.

Figure 13:
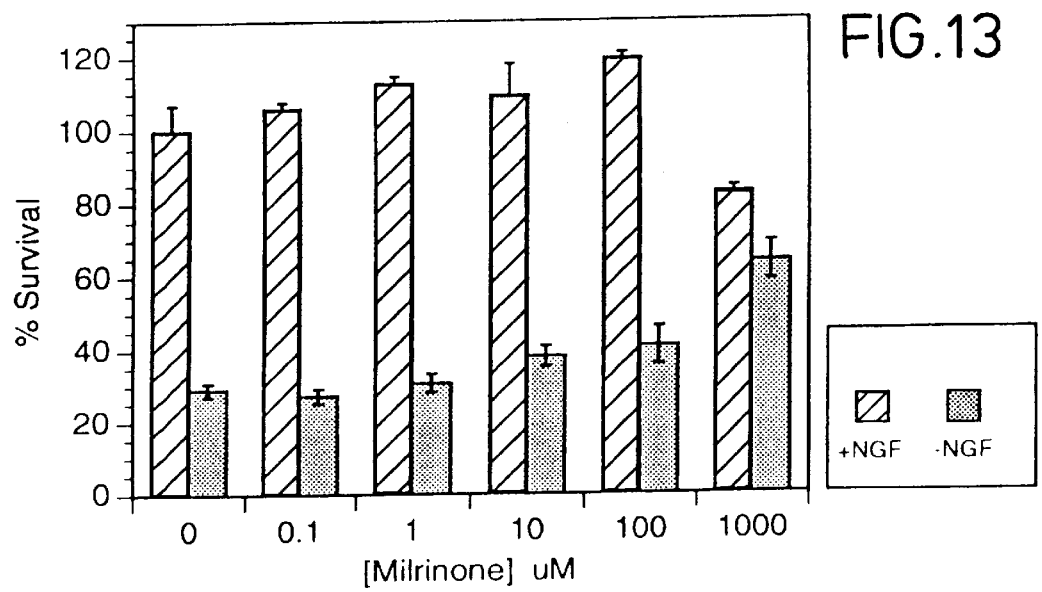
FIG. 13 relates to Example 12 and is a bar chart showing that milrinone promotes cell survival in conditions leading to apoptosis.

EXAMPLE 11
Milrinone Promotes Cell Survival in Conditions leading to Apoptosis The experiment of Example 2 was repeated, except that various concentrations of milrinone were used in place of serotonin. The results are shown in FIG. 13.

Figure 14:
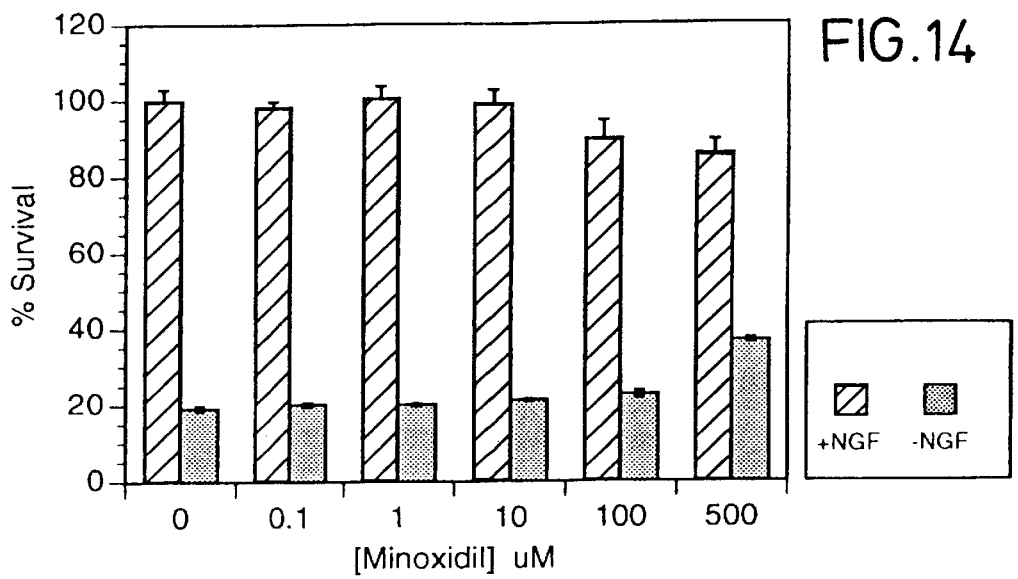
FIG. 14 relates to Example 13 and is a bar chart showing that minoxidil sulphate promotes cell survival in conditions leading to apoptosis.

EXAMPLE 12
Minoxidil Sulphate Promotes Cell Survival in Conditions leading to Apoptosis The experiment of Example 2 was repeated, except that various concentrations of minoxidil sulphate were used in place of serotonin. The results are shown in FIG. 14.

Figure 15:
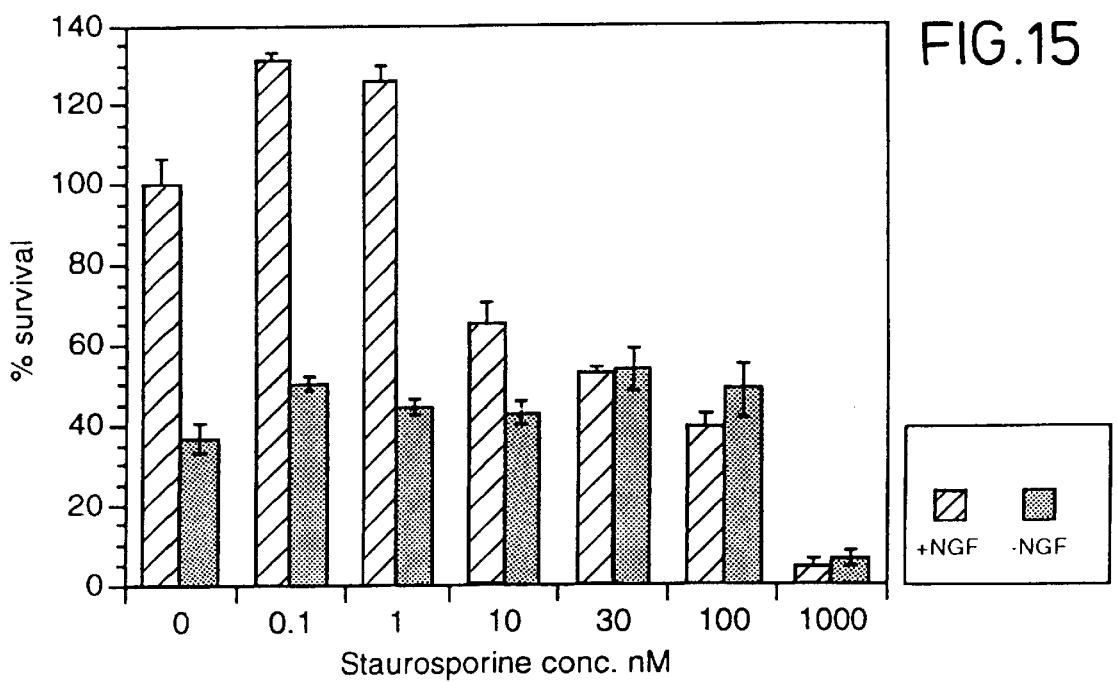
FIG. 15 relates to the Additional Experiment and shows that staurosporine induces a dose-dependent decrease in survival of differentiated PC12 cells in the presence of NGF.

ADDITIONAL EXPERIMENT
Staurosporine Induces Apoptosis and $p34^{cdc2}$ Kinase Staurosporine has been reported to cause the rapid death by apoptosis of a number of cell types (e.g. Jacobson et al., *Nature* 361 365 (1993); Falcieri et al., *Biochem. Biophys. Res. Commun.* 193 19 (1993); Bertrand et al., *Exp. Cell Res.* 207 388 (1993)). It now appears that this compound induces a dose-dependent decrease in survival of differentiated PC12 cells in the presence of NGF (FIG. 15). When nuclear morphology was analysed by propidium iodide staining, extensive chromatin condensation was observed, indicating that death in these cells is occurring by the process of apoptosis.

Figure 16:
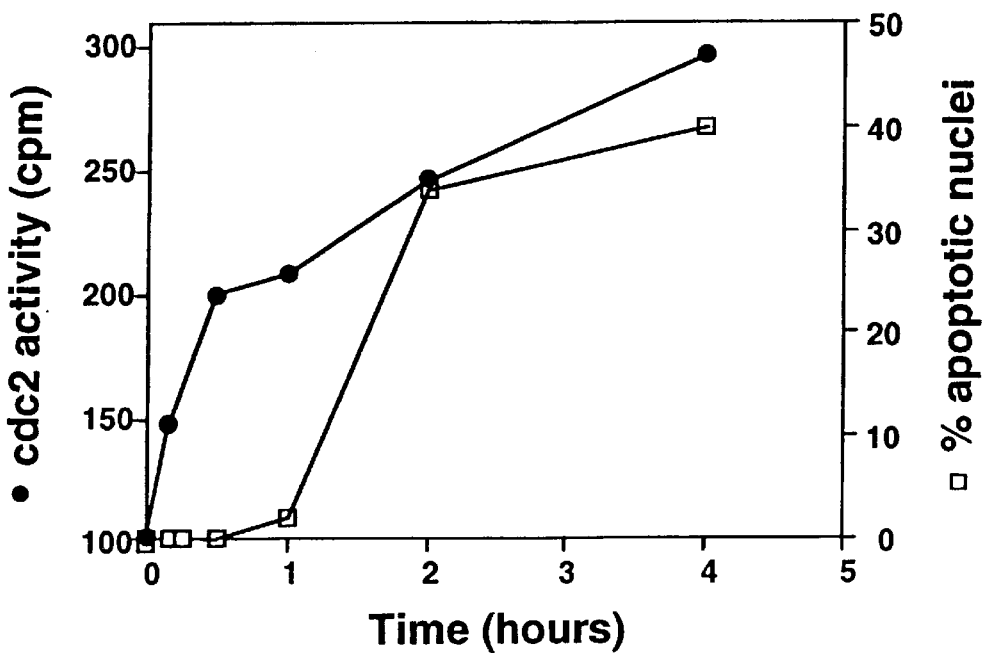
FIG. 16 relates to the Additional Experiment and shows the effect of staurosporine on cdc2 activity and cell death in PC12 cells.

Since activation of the cell cycle regulated kinase $p34^{cdc2}$ accompanies the induction of death due to NGF withdrawal in these cells, the question of whether staurosporine-induced death of PC12 cells also results in the activation of this enzyme was investigated. Addition of staurosporine (1 μM) to differentiated PC12 cells activated $p34^{cdc2}$ within 5 min, which continued to increase over the 4 h time period. The first evidence of pyknotic nuclei was not observed until 2 h after staurosporine addition, and therefore indicates that activation of this kinase clearly precedes chromatin condensation (FIG. 16).

Figure 19:
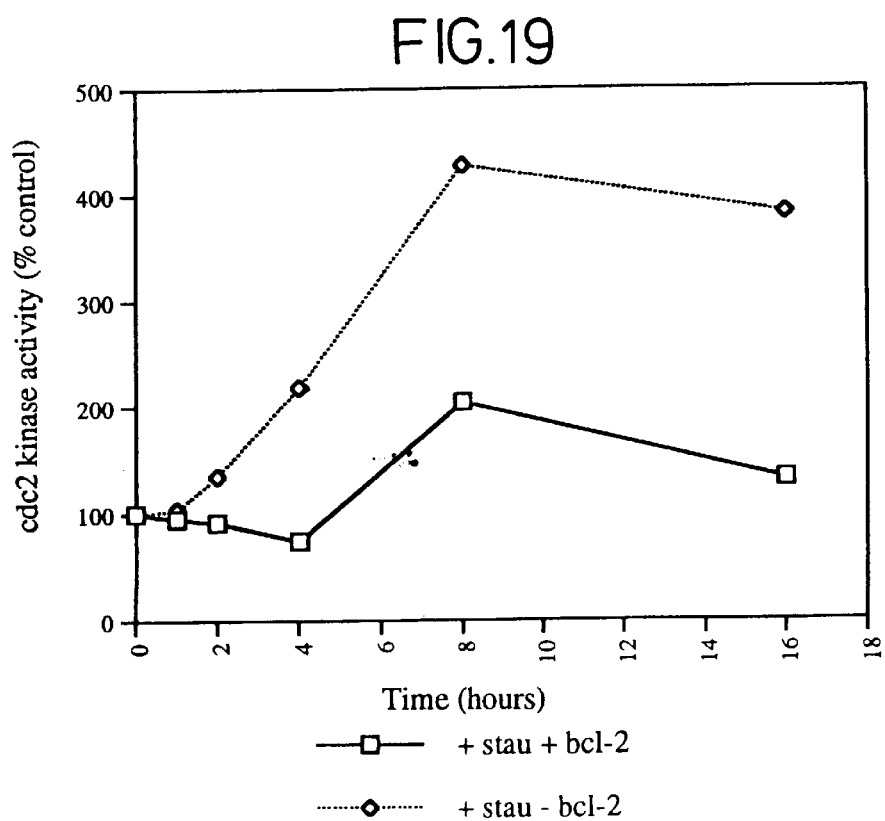
FIG. 19 relates to the Additional Experiment and shows the effect of the bcl-2 overexpression on staurosporine-induced cdc2 kinase activity in quiescent Swiss 3T3 fibroblasts.
Figure 17:
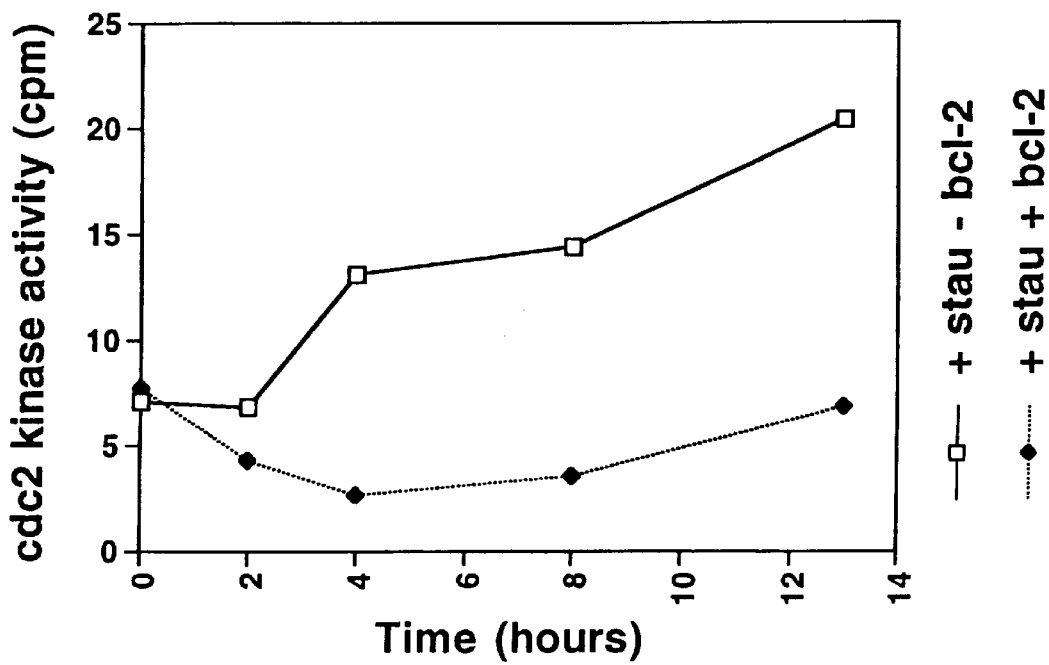
FIG. 17 relates to the Additional Experiment and shows the effect of overexpression of bcl-2 on staurosporine-induced cdc2 kinase activity in proliferating human fibroblasts.
Figure 18A:
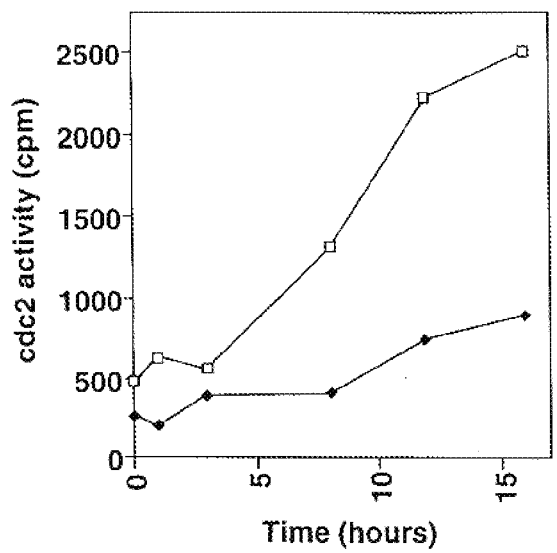
FIGS. 18A and 18B relates to the Additional Experiment and shows the effect of bcl-2 overexpression on activation of cdc2 induced by staurosporine in quiescent rat1 fibroblasts.
Figure 18B:
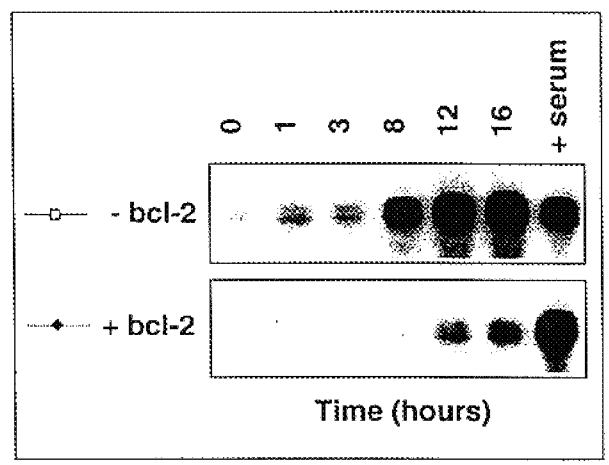

It has been shown that staurosporine causes death of fibroblasts and that overexpression of the protein bcl-2 can substantially delay this effect (Jacobson et al *Nature* 361, 365 (1993)). Staurosporine treatment of either proliferating (FIG. 17), or serum-deprived rat1 (FIGS. 18A and 18B) or Swiss 3T3 (FIG. 19) fibroblasts also causes activation of $p34^{cdc2}$, which is significantly reduced if these cells are forced to overexpress bcl-2 (FIGS. 17, 18A & B and 19). This could suggest that bcl-2 lies upstream of $p34^{cdc2}$ in the death pathway, and indicate a potential mechanism for the action of cbl-2.

Overall, these results demonstrate that activation of $p34^{cdc2}$ is often a part of the apoptotic pathway in both serum-deprived and proliferating cells. These data are reinforced by the recent observation that both cytotoxic T-lymphocyte- and staurosporine-induced death of target cells also involves activation of this kinase (Shi et al., *Science* 263 1143 (1994). Since staurosporine is a general kinase inhibitor, the ability of this compound to induce both death and activation of the kinase $p34^{cdc2}$ is especially important.

What is claimed is:

1. A method of treating or preventing a neurodegenerative disease involving apoptotic cell death, the method comprising administering to a subject in need thereof, or to cells of a subject, an effective amount of an agent which prevents cell entry into, or passage through, the mitotic cycle, wherein the agent prevents or inhibits cyclin synthesis as identified by a reporter gene assay using the cyclin promoter, or an enzymatic assay for cdc2 or cdk2 activation or cdc2 or cdk2 activity, and wherein the cell death occurs in non-dividing cells; provided that the agent is not bFGF, IGF-I, IGF-II, potassium ions or a cAMP-elevating agent.

2. A method as claimed in claim 1, wherein the gent prevents or inhibits the activation of $p34^{cdc2}$ as identified by an enzymatic assay for an activator of $p34^{cdc2}$.

3. A method as claimed in claim 1, wherein the agent is a promoter or activator of wee1 or mik1 as identified by an enzymatic assay for an activator of wee1 or mik1.

4. A method as claimed in claim 1, wherein the agent is an inhibitor of cdc25 as identified by an enzymatic assay for cdc25 activity.

5. A method as claimed in claim 1, wherein the agent is an inhibitor of cyclin B as identified by an enzymatic assay for cyclin B activity.

6. A method as claimed in claim 1, wherein the agent is serotonin, dopamine, ascorbic acid, gliquidone, caffeine, hydrocortisone or dexamethasone.

7. A method as claimed in claim 1, wherein the non-driving cells are neurons.

8. A method as claimed in claim 7, which is a method for the treatment or prophylaxis of Alzheimer's disease, Parkinson's disease, motor-neuron disease, or neuronal cell death in stroke.

9. A method as claimed in claim 1, wherein the agent is administered orally.

10. A method of treating or preventing a neurodegenerative disease involving apoptotic cell death, the method comprising administering to a subject in need thereof, or to cells of a subject, an effective amount of 6-dimethylaminopurine (6-DMAP) or an analogue thereof which prevents cell entry into, or passage through, the mitotic cycle and wherein the cell death occurs in non-dividing cells.

11. A method of preventing apoptotic cell death, the method comprising administering to cells an effective amount of an agent, other than bFGF, IGF-I, IGF-II, potassium ions or a cAMP-elevating agent, which prevents cell entry in to the mitotic cycle, wherein the agent prevents or inhibits cyclin synthesis as identified by a reporter gene assay using the cyclin promoter, or an enzymatic assay for cdc2 or cdk2 activation or cdc2 or cdk2 activity, and wherein the cell death occurs in non-dividing cells.

12. A method of preventing apoptotic cell death in a research model, the method comprising administering to cells an effective amount of an agent which prevents cell entry into, or passage through, the mitotic cycle, wherein the agent prevents or inhibits cyclin synthesis as identified by a reporter gene assay using the cyclin promoter, or an enzymatic assay for cdc2 or cdk2 activation or cdc2 or cdk2 activity, and wherein the cell death occurs in non-dividing cells; provided that the agent is not bFGF, IGF-I or IGF-II, potassium ions or a cAMP-elevating agent.

13. The method as claimed in claim 12, wherein the research model is on the etiology of cell death.

14. The method as claimed in claim 12, wherein the method further comprises using the agent to prevent or inhibit cyclin synthesis or cdc2 or cdk2 activation or cdc2 or cdk2 activity.

15. A method as claimed in claim 12, wherein the agent prevents or inhibits the activation of $p34^{cdc2}$.

16. A method as claimed in claim 12, wherein the agent is 6-dimethylaminopurine (6-DMAP) or an analogue thereof.

17. A method as claimed in claim 12, wherein the agent is a promoter or activator of wee1 or mik1.

18. A method as claimed in claim 12, wherein the agent is an inhibitor of cdc25.

19. A method as claimed in claim 12, wherein the agent is an inhibitor of cyclin B.

20. A method as claimed in claim 12, wherein the agent is serotonin, dopamine, ascorbic acid, gluquidone, caffeine, hydrocortisone or dexamethasone.

21. A method as claimed in claim 12, wherein the non-dividing cells are muscle cells.

22. A method as claimed in claim 12, wherein the non-dividing cells are neurons.

* * * * *